US00PP34471P2

(12) United States Plant Patent
Danziger

(10) Patent No.: US PP34,471 P2
(45) Date of Patent: Aug. 2, 2022

(54) ***IMPATIENS* PLANT NAMED 'DNGISLWHTE'**

(50) Latin Name: *Impatiens hawkeri*
Varietal Denomination: 'DNGISLWHTE'

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/587,186

(22) Filed: Jan. 28, 2022

(51) Int. Cl.
*A01H 5/02* (2018.01)
*A01H 6/16* (2018.01)

(52) U.S. Cl.
USPC ..... Plt./318.2
CPC ..... *A01H 6/165* (2018.05)

(58) Field of Classification Search
USPC ..... Plt./318.2
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Impatiens* plant named 'DNGISLWHTE' is disclosed, characterized by large, white flowers on well-branched plants with sun resistance. The new variety is an *Impatiens*, normally produced as an outdoor garden or container plant.

2 Drawing Sheets

Latin name of the genus and species: *Impatiens hawkeri.*
Variety denomination: 'DNGISLWHTE'.

BACKGROUND OF THE INVENTION

The new *Impatiens* cultivar is the product of a planned breeding program conducted by the inventor, Gavriel Danziger, in Moshav Mishmar Hashiva, Israel. The objective of the breeding program was to produce new *Impatiens* varieties for ornamental commercial applications. The crossing resulting in this new variety was made in April of 2016.

The seed parent is an unpatented, proprietary *Impatiens hawkeri* 'BM-Z-175'. The pollen parent is the *Impatiens hawkeri* proprietary line identified by code 'BM-15-767' (unpatented). The new variety was selected in February of 2017, at a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in February of 2017, and has shown that the unique features of this cultivar are stable and reproduced true to type in multiple successive generations.

SUMMARY OF THE INVENTION

The cultivar 'DNGISLWHTE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DNGISLWHTE' These characteristics in combination distinguish 'DNGISLWHTE' as a new and distinct *Impatiens* cultivar:

1. Large flowers.
2. White Flowers.
3. Well-branched plants.
4. Sun resistance.

PARENTAL COMPARISON

Plants of the new cultivar 'DDNGISLWHTE' are similar to plants of the seed parent in most horticultural characteristics, however, plants of the new cultivar 'DNGISLWHTE' differ in the following;

1. Plants of the new variety have a more controlled plant habit than plants of the seed parent.
2. Flowers of the new variety are larger than flowers of the seed parent.

Plants of the new cultivar 'DNGISLWHTE' are similar to plants of the pollen parent in most horticultural characteristics, however, plants of the new cultivar 'DNGISLWHTE' differ in the following;

1. Plants of the new variety are more vigorous than plants of the pollen parent.
2. Flowers of the new variety are lighter colored white than flowers of the pollen parent.

COMMERCIAL COMPARISON

Plants of the new cultivar 'DNGISLWHTE' can be compared to the commercial variety *Impatiens hawkeri* 'SAKIMP027', U.S. Plant Pat. No. 24,320. These varieties are similar in most horticultural characteristics, however, plants of the new cultivar 'DNGISLWHITE' differ in the following;

1. Foliage of the new variety is larger than foliage of this comparator variety.
2. Plants of the new variety are more compact than plants of this comparator.

Plants of the new cultivar 'DNGISLWHTE' can be compared to the commercial variety *Impatiens hawkeri* 'SAKIMP018', U.S. Plant Pat. No. 21,768. These varieties are similar in most horticultural characteristics, however, plants of the new cultivar 'DNGISLWHITE' differ in the following;

1. Plants of the new variety are more compact than plants of this comparator.
2. The new variety produces larger foliage than this comparator.
3. Foliage of the new variety is solid green; foliage of this comparator is variegated yellow and green.

BRIEF DESCRIPTION OF THE PHOTOGRAPHS

The accompanying photographs illustrate the overall appearance of the new *Impatiens hawkeri* 'DNGISLWHTE' showing the colors as true as is reasonably possible with colored reproductions of this type. Colors in the photographs may differ slightly from the color values cited in the detailed botanical description which accurately describes the color of 'DNGISLWHTE'.

DETAILED BOTANICAL DESCRIPTION

Figure 1:
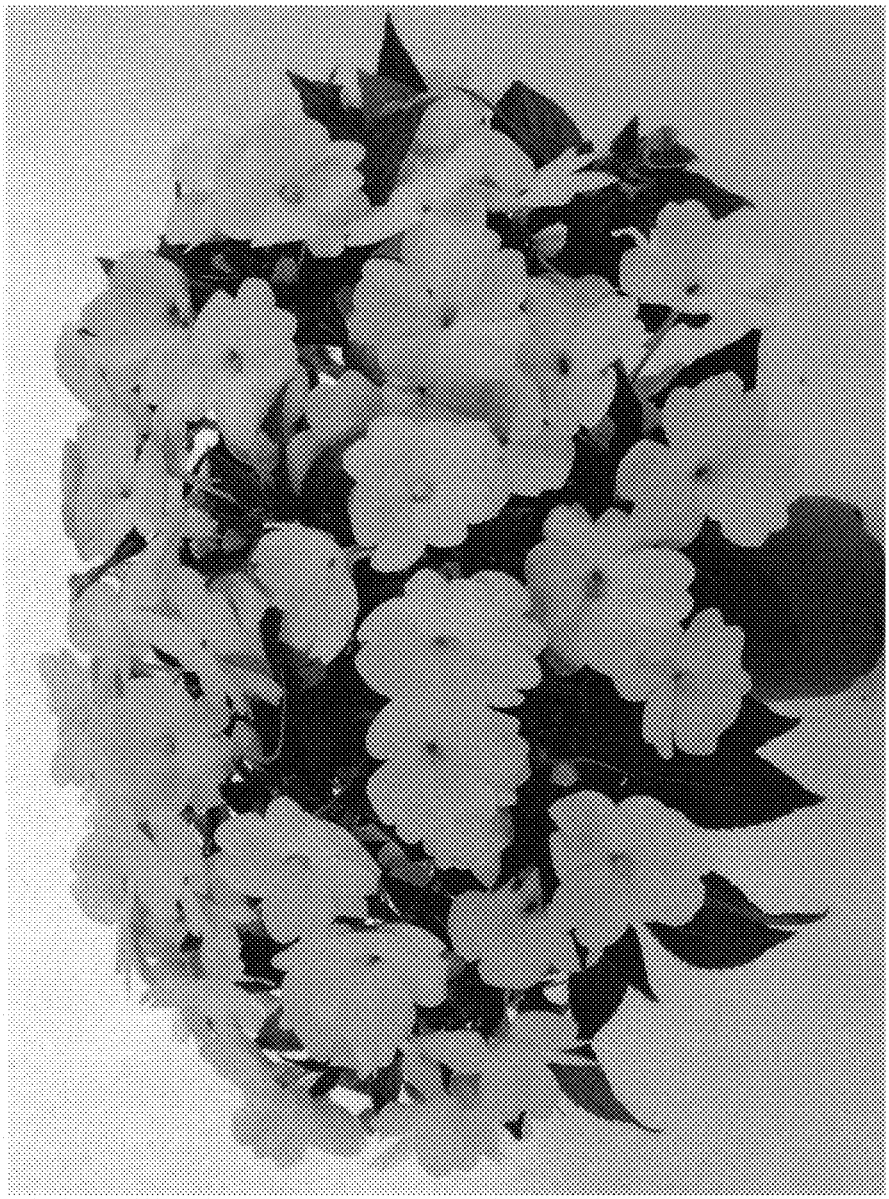
FIG. 1 shows a side view perspective of a typical flowering plant of 'DNGISLWHTE', at approximately 12 weeks old.
Figure 2:
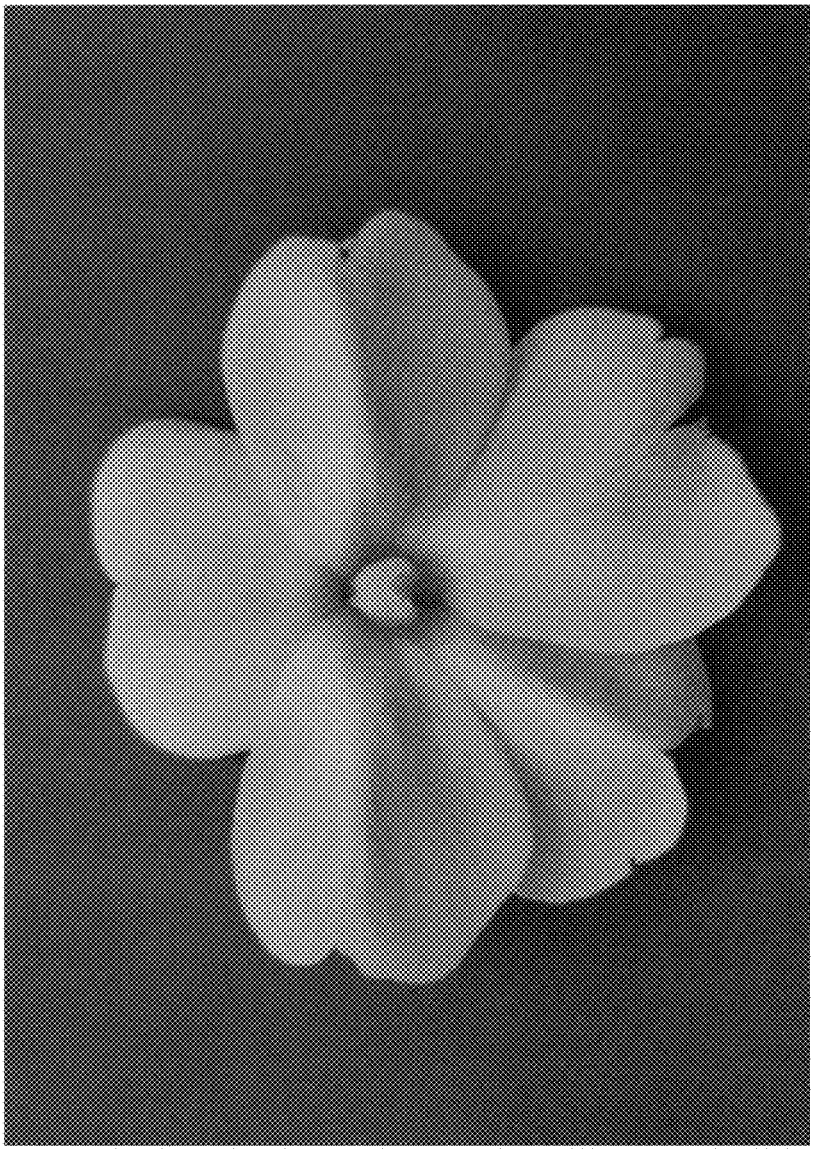
FIG. 2 shows a close-up view of a typical flower of 'DDNGISLWHTE'.

In the following description, color references are made to The Royal Horticultural Society Mini Colour Chart 2005, except where general terms of ordinary dictionary significance are used. The following observations and measurements describe 'DNGISLWHTE' plants grown from autumn to spring in moderate climate in a greenhouse, in Moshav Mishmar Hashiva, Israel. General light conditions are bright, normal sunlight. Measurements and numerical values represent averages of typical plant types. Age of the plants described is approximately 12 weeks from a rooted cutting.

Botanical classification: *Impatiens hawkeri* 'DNGISLWHTE'.

PROPAGATION

Type of propagation typically used: Vegetative cuttings.

Time to initiate roots: 10 to 14 days at approximately 24° C.

Root description: Moderately dense and fibrous. Medium brown in color, not accurately measured with R.H.S. chart.

PLANT

Growth habit: Mounded.

Pot size of plant described: 12 cm.

Height: 25 to 30 cm.

Plant spread: 40 cm.

Growth rate: Moderate.

Branching characteristics: Well-branched.

Length of primary lateral branches: 20 to 25 cm.

Quantity of primary lateral branches: 5 to 10.

Characteristics of primary lateral branches:

- *Form*.—Ovate.
- *Diameter*.—1 cm.
- *Color*.—Near RHS Yellow-Green 147 C.
- *Texture*.—Smooth.
- *Strength*.—Strong, very sturdy.

Internode length: 5 to 8 cm.

FOLIAGE

Leaf:

- *Arrangement*.—Alternate.
- *Quantity*.—Approximately 25 to 30 per branch.
- *Average length*.—9 cm.
- *Average width*.—4 cm.
- *Shape of blade*.—Lanceolate.
- *Apex*.—Apiculate.
- *Base*.—Acuminate.
- *Margin*.—Ciliate.
- *Texture*.—Smooth.
- *Angle of attachment*.—45 degrees from stem.
- *Color*.—Young foliage upper side: Near RHS Green 137A. Young foliage under side: Near RHS Yellow-Green 146B. Mature foliage upper side: Near RHS Green N137A. Mature foliage under side: Near RHS Yellow-Green 147B.
- *Venation*.—Type: Pinnate. Venation color upper side: Near RHS Yellow-Green 147D. Venation color under side: Near RHS Yellow-Green 147D.
- *Petiole*.—Length: 1 to 1.5 cm. Diameter: 0.5 cm. Color: Near RHS Yellow-Green 145D. Texture: Smooth.

FLOWER

Natural flowering season: Flowers at any day length. All year round in a greenhouse environment. Flowering is continuous from spring until fall in an outdoor garden.

Days to flowering from rooted cutting: 10 weeks.

Inflorescence and flower type and habit: Single flowers raised above the foliage. The corolla consists of five petals.

Rate of flower opening: 10 to 15 days from bud to fully opened flower.

Flower longevity on plant: 5 to 8 days.

Persistent or self-cleaning: Self-cleaning.

Bud:

- *Shape*.—Ovate.
- *Length*.—1.5 cm.
- *Diameter*.—About 1 cm.
- *Color*.—Near RHS White N155A.

Flower size:

- *Diameter*.—6.5 cm.
- *Depth*.—1 cm.

Petals:

- *Quantity*.—5.
- *Arrangement*.—Overlapping whorl.
- *Length*.—3 cm.
- *Width*.—2.5 to 3 cm.
- *Shape*.—Obcordate.
- *Apex*.—Heart Shape.
- *Base*.—Acute.
- *Margin*.—Entire.
- *Texture, upper and lower surfaces*.—Smooth.
- *Color*.—When opening, upper surface: Near RHS White NN155D. When opening, lower surface: Near RHS White NN155D. Fully opened, upper surface: Near RHS White NN155D. Fully opened, lower surface: Near RHS White NN155D.

Spurs:

- *Quantity per flower*.—1.
- *Length*.—7 cm.

*Diameter.*—0.2 cm.
*Aspect.*—Spur curvature 40° to 45° from peduncle.
*Color.*—Towards base: Near RHS Yellow-Green 149D. Apex: Near RHS Yellow-Green 149B.

Sepals:
*Quantity.*—2.
*Length.*—1 to 1.5 cm.
*Width.*—0.6 cm.
*Shape* (*overall*).—Oblong. Apex: Caudate. Base: Rounded.
*Margin.*—Entire.
*Color.*—Near RHS Yellow-Green 145D.

Peduncles:
*Length.*—5 to 5.5 cm.
*Diameter.*—0.3 cm.
*Angle.*—About 45° to the lateral branch.
*Strength.*—Sturdy, flexible.
*Texture.*—Smooth.
*Color.*—Near RHS Yellow-Green 145C.

Fragrance: None.

REPRODUCTIVE ORGANS

Stamens: 5 stamens with anthers that are more or less fused and form a cap over the ovary.

Anthers:
*Shape.*—Oblong.
*Length.*—Approximately 0.5 cm.
*Color.*—Near RHS White 155B.
*Pollen.*—No pollen.

Pistil:
*Number.*—1.
*Length.*—0.4 cm.
*Style.*—Length: 0.4 cm. Color: Near RHS Yellow-Green 144C.
*Stigma.*—Shape: Globular. Color: Near RHS Yellow-Green 149D.

OTHER CHARACTERISTICS

Seeds and fruits: 5 to 10 seeds per fruit.

Disease/pest resistance: Neither resistance nor susceptibility to normal diseases and pests of *Impatiens* has been observed.

Temperature tolerance: Tolerant at 30° C. and 10° C. (grows best at 18° C.-25° C.).

Drought tolerance: Not tolerant to drought.

What is claimed is:

1. A new and distinct cultivar of *Impatiens* plant named 'DNGISLWHTE' as herein illustrated and described.

* * * * *